US010123749B2

(12) United States Patent
Kamimura

(10) Patent No.: US 10,123,749 B2
(45) Date of Patent: Nov. 13, 2018

(54) BLOOD SUGAR LEVEL PREDICTION DEVICE, MEASUREMENT DEVICE, BLOOD SUGAR LEVEL PREDICTION METHOD AND COMPUTER-READABLE STORAGE MEDIUM

(71) Applicant: NEC Solution Innovators, Ltd., Tokyo (JP)

(72) Inventor: Ippei Kamimura, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 502 days.

(21) Appl. No.: 14/648,339

(22) PCT Filed: Oct. 30, 2013

(86) PCT No.: PCT/JP2013/079441
§ 371 (c)(1),
(2) Date: May 29, 2015

(87) PCT Pub. No.: WO2014/087768
PCT Pub. Date: Jun. 12, 2014

(65) Prior Publication Data
US 2015/0297144 A1    Oct. 22, 2015

(30) Foreign Application Priority Data

Dec. 4, 2012  (JP) ................ 2012-265283

(51) Int. Cl.
*A61B 5/1455* (2006.01)
*A61B 5/00* (2006.01)
(Continued)

(52) U.S. Cl.
CPC .......... *A61B 5/7275* (2013.01); *A61B 5/1455* (2013.01); *A61B 5/14532* (2013.01);
(Continued)

(58) Field of Classification Search
None
See application file for complete search history.

(56) References Cited

U.S. PATENT DOCUMENTS

| 5,840,020 A | 11/1998 | Heinonen et al. |
| 2003/0208113 A1 | 11/2003 | Mault et al. |

(Continued)

FOREIGN PATENT DOCUMENTS

| CN | 1422136 A | 6/2003 |
| JP | H11-296598 A | 10/1999 |

(Continued)

OTHER PUBLICATIONS

Written Opinion issued by The Intellectual Property Office of Singapore for Application No. 11201504149Q dated Jul. 8, 2016 (4 pages).

(Continued)

Primary Examiner — Eric Winakur
Assistant Examiner — Marjan Fardanesh
(74) Attorney, Agent, or Firm — Wilmer Cutler Pickering Hale and Dorr LLP

(57) ABSTRACT

A blood sugar level prediction device (10) is for predicting the blood sugar level of a user (30). The blood sugar level prediction device (10) is provided with a pattern selection unit (11) that selects one pattern from a plurality of preset blood sugar level time series variation patterns, based on the blood sugar level of the user (30) at the time of fasting, and a correction processing unit (12) that corrects the selected pattern using a plurality of measured values obtained by executing optical measurement of blood sugar levels over a number of measurement dates, targeting the user (30).

10 Claims, 6 Drawing Sheets

(51) Int. Cl.
*G06Q 50/22* (2018.01)
*A61B 5/145* (2006.01)
*G06F 19/00* (2018.01)
*G06Q 10/10* (2012.01)

(52) U.S. Cl.
CPC .......... *A61B 5/4866* (2013.01); *A61B 5/7278* (2013.01); *G06F 19/00* (2013.01); *G06Q 10/10* (2013.01); *G06Q 50/22* (2013.01); *A61B 2560/0238* (2013.01)

(56) References Cited

U.S. PATENT DOCUMENTS

| 2009/0006061 A1 | 1/2009 | Thukral et al. |
| 2010/0174553 A1 | 7/2010 | Kaufman et al. |

FOREIGN PATENT DOCUMENTS

| JP | 2000-503556 A | 3/2000 |
| JP | 2001-188772 A | 7/2001 |
| JP | 2001-212114 A | 8/2001 |
| JP | 2001-221803 A | 8/2001 |
| JP | 2002-298281 A | 10/2002 |
| JP | 2003-144421 A | 5/2003 |
| WO | WO-97/28737 | 8/1997 |
| WO | WO-2006/009199 A1 | 1/2006 |

OTHER PUBLICATIONS

Written Opinion dated Jul. 8, 2016 issued by The Intellectual Property Office of Singapore for Application No. 11201504149Q on Jul. 11, 2016 (7 pages).
Chinese Office Action issued by the State Intellectual Property Office of People's Republic of China for Chinese Application No. 201380063886.8 dated Jun. 1, 2017 (18 pages).
Japanese Office Action issued by the Japan Patent Office for Japanese Application No. 2012-265283 dated Dec. 11, 2013 (6 pages).
International Search Report corresponding to PCT/JP2013/079441, dated Dec. 17, 2013, 2 pages.
International Written Opinion issued in corresponding Singapore Application No. 11201504149Q, dated Nov. 11, 2015, 7 pages.

BLOOD SUGAR LEVEL PREDICTION DEVICE, MEASUREMENT DEVICE, BLOOD SUGAR LEVEL PREDICTION METHOD AND COMPUTER-READABLE STORAGE MEDIUM

CROSS-REFERENCE TO RELATED APPLICATIONS

This application is a national stage application of International Application No. PCT/JP2013/079441 entitled "BLOOD SUGAR LEVEL PREDICTION DEVICE, MEASUREMENT DEVICE, BLOOD SUGAR LEVEL PREDICTION METHOD AND COMPUTER-READABLE STORAGE MEDIUM," filed on Oct. 30, 2013, which claims the benefit of the priority of Japanese Patent Application No. 2012-265283, filed on Dec. 4, 2012, the disclosures of each of which are hereby incorporated by reference in their entirety.

TECHNICAL FIELD

The present invention relates to a blood sugar level prediction device and a blood sugar level prediction method that are for predicting the blood sugar level of a user, and further relates to a measurement device that uses the blood sugar level prediction device and method and a computer-readable storage medium storing a computer program for realizing the blood sugar level prediction device and method.

BACKGROUND ART

Generally, in people with diabetes, the concentration of glucose in the blood exceeds a certain level, resulting in excessive thirst and increased urination, and, in extreme cases, impaired consciousness and coma. It is thus important for diabetics to have a grasp of their own blood sugar level.

However, the concentration of glucose in a person's blood, that is, his or her blood sugar level, changes throughout the day. Specifically, when a person is fasting, his or her blood sugar level keeps falling for as long as he or she does not eat, and then when the person eats, his or her blood sugar level rises. Accordingly, in order for a person to have a grasp of his or her exact blood sugar level, the person needs to measure his or her blood sugar level repeatedly during the day. Accordingly, many diabetics manage their blood sugar level by measuring their own blood sugar level with a portable glucometer.

It does, however, become burdensome for diabetics to measure their blood sugar level repeatedly during the day in this way. Also, if blood sugar levels are not adequately measured, it is difficult for a doctor to determine the insulin dose.

Thus, in order to reduce the burden on diabetics and to make it easier to determine the insulin dose, Patent Document 1, for example, discloses a method for predicting the change in a diabetic's blood sugar level. Specifically, the method disclosed in Patent Document 1 focuses on the fact that the behavior of blood sugar levels over time is a chaos phenomenon, and uses the current blood sugar level to predict blood sugar levels from the next day on with a local fuzzy reconstruction method based on blood sugar level time series data.

Because subsequent blood sugar levels can be predicted simply by firstly acquiring blood sugar level time series data, the method disclosed in Patent Document 1 can conceivably reduce the burden on diabetics and make it easier to determine the insulin dose.

LIST OF PRIOR ART DOCUMENTS

Patent Document

Patent Document 1: JP 11-296598A

DISCLOSURE OF THE INVENTION

Problems to be Solved by the Invention

However, the method disclosed in Patent Document 1 initially requires preparation of a large number of measured values. Also, in order to enhance accuracy, the interval at which measured values are acquired needs to be shortened as much as possible. In view of these points, the method disclosed in Patent Document 1 conceivably has little effect in reducing the burden on diabetics.

An exemplary object of the present invention is to solve the above problems and provide a blood sugar level prediction device, a measurement device, a blood sugar level prediction method and a computer program that enable the user's blood sugar level to be correctly predicted while reducing the burden on the user at the time of blood sugar level measurement.

Means for Solving the Problems

In order to achieve the above object, a blood sugar level prediction device of the present invention is a device for predicting a user's blood sugar level, including a pattern selection unit that selects one pattern from a plurality of preset blood sugar level time series variation patterns, based on a blood sugar level at a fasting time of the user, and a correction processing unit that corrects the selected pattern using a plurality of measured values obtained by executing optical measurement of blood sugar levels over a number of measurement dates, targeting the user.

Also, in order to achieve the above object, a measurement device of the present invention is a measurement device that measures the user's blood sugar level though optical measurement, including a measurement unit that executes the optical measurement, a standard curve database that stores a standard curve for converting a measured value that is obtained by executing the optical measurement into a blood sugar level, for each size of corresponding blood sugar levels, a control processing unit that calculates a blood sugar level by selecting one of the standard curves and applying the measured value obtained by executing the optical measurement to the selected standard curve, and a blood sugar level prediction unit that predicts the blood sugar level of the user by selecting one pattern from a plurality of preset blood sugar level time series variation patterns, based on a blood sugar level at a fasting time of the user, and correcting the selected pattern using a plurality of measured values obtained by executing the optical measurement over a number of measurement dates, targeting the user, the control processing unit, in a case where selection and correction of the pattern have been executed by the blood sugar level prediction unit, predicting the blood sugar level using the corrected pattern and selecting the standard curve based on the predicted blood sugar level.

Furthermore, in order to achieve the above object, a blood sugar level prediction method of the present invention is a method for predicting a user's blood sugar level, having the steps of (a) selecting one pattern from a plurality of preset blood sugar level time series variation patterns, based on a blood sugar level at a fasting time of the user, and (b) correcting the selected pattern using a plurality of measured values obtained by executing optical measurement of blood sugar levels over a number of measurement dates, targeting the user.

In order to achieve the above object, a computer-readable storage medium of the present invention is a computer-readable storage medium storing a computer program for predicting a blood sugar level of a user by computer, the program including a command that causes the computer to execute the steps of (a) selecting one pattern from a plurality of preset blood sugar level time series variation patterns, based on a blood sugar level at a fasting time of the user, and (b) correcting the selected pattern using a plurality of measured values obtained by executing optical measurement of blood sugar levels over a number of measurement dates, targeting the user.

Advantageous Effects of the Invention

According to the present invention as described above, the user's blood sugar level can be correctly predicted, while reducing the burden on the user at the time of blood sugar level measurement.

MODE FOR CARRYING OUT THE INVENTION

Embodiments

Figure 1:
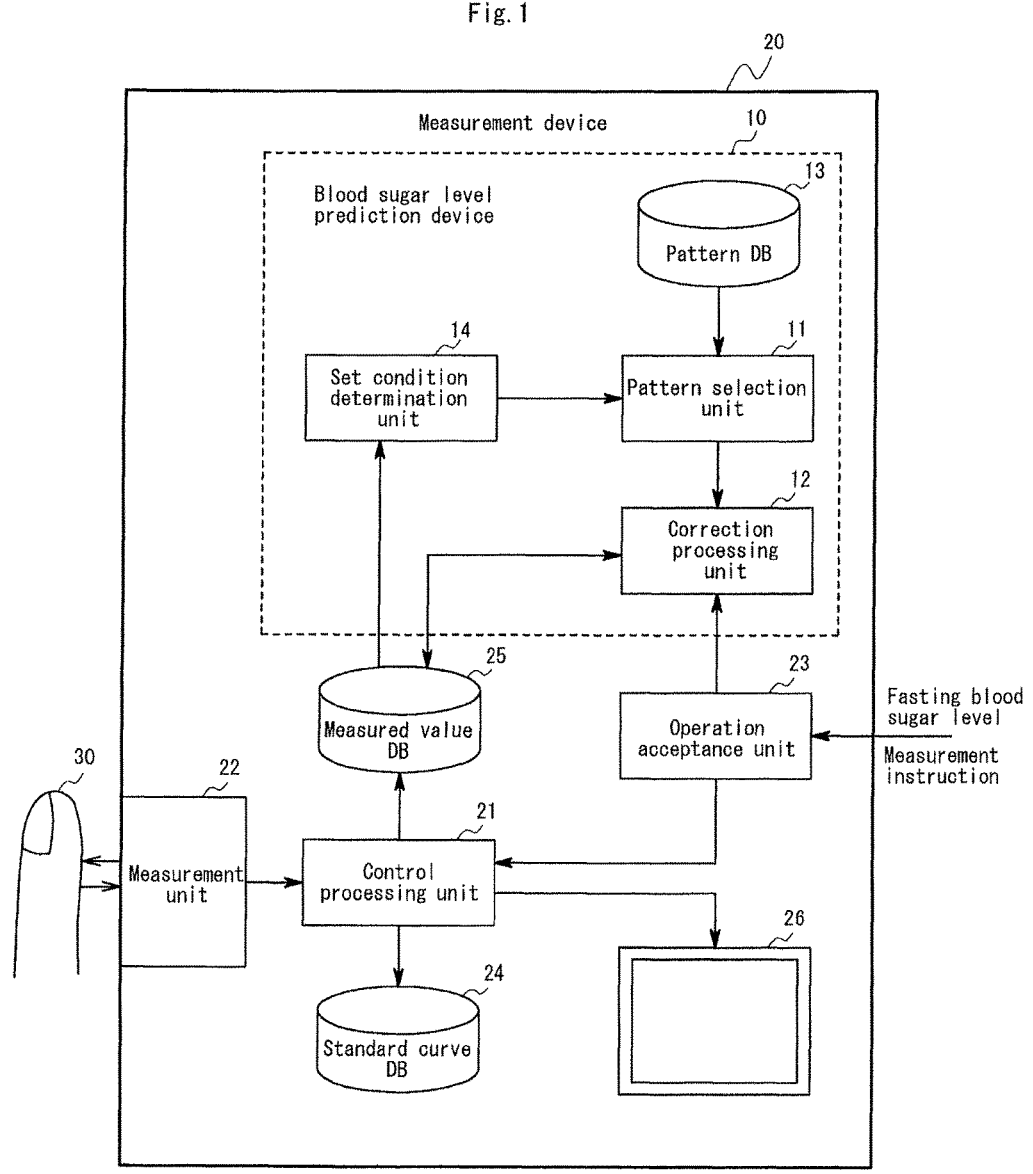
FIG. 1 is a block diagram showing the configurations of a blood sugar level prediction device and a measurement device in an embodiment of the present invention.

Hereinafter, a blood sugar level prediction device, a measurement device, a blood sugar level prediction method and a computer program in an embodiment of the present invention will be described, with reference to FIGS. 1 to 6.
Device Configuration Initially, the configurations of a blood sugar level prediction device 10 and a measurement device 20 of the present embodiment will be described using FIG. 1. FIG. 1 is a block diagram showing the configurations of the blood sugar level prediction device and the measurement device of the present embodiment.

First, the configuration of the blood sugar level prediction device of the present embodiment will be described. As shown in FIG. 1, the blood sugar level prediction device 10 is provided with a pattern selection unit 11 and a correction processing unit 12, and predicts the blood sugar level of a user 30 with these units. Of these, the pattern selection unit 11 selects, from a plurality of blood sugar level time series variation patterns (hereinafter referred to as "time series variation patterns") that have been set in advance, one time series variation pattern, based on the blood sugar level of the user 30 when he or she is fasting (hereinafter referred to as the "fasting blood sugar level"). Note that, hereinafter, the selected time series variation pattern will be referred to as the "initial pattern".

The correction processing unit 12 first acquires a plurality of measured values, which are obtained by measuring the blood sugar level of the user 30 optically over a number of measurement dates. The correction processing unit 12 then corrects the initial pattern using the plurality of acquired measured values.

Thus, with the blood sugar level prediction device 10, a time series variation pattern considered to be the closest to the time series variation in the blood sugar level of the user 30 is selected based on the blood sugar level of the user 30 at the time of fasting. Because this selected time series variation pattern (initial pattern) is corrected using actual measured values, the pattern will be aligned with the actual condition of the user 30. Also, the user 30 need only input his or her blood sugar level at the time of fasting, and measure his or her blood sugar level optically several times over a number of measurement dates. In other words, according to the blood sugar level prediction device 10, the blood sugar level of the user 30 can be correctly predicted, while reducing the burden on the user 30.

Here, the configuration of the blood sugar level prediction device 10 will be further specifically described using FIG. 1. First, in the present embodiment, the blood sugar level prediction device 10 is a part of the measurement device 20, as shown in FIG. 1, and functions as a blood sugar level prediction unit. The measurement device 20 is a device that optically measures the user's blood sugar level, as will be discussed later.

In the present embodiment, the blood sugar level prediction device 10 is provided with a pattern database 13 that stores a plurality of time series patterns and a setting condition determination unit 14, in addition to the pattern selection unit 11 and the correction processing unit 12 that were mentioned above. Furthermore, the blood sugar level prediction device 10 is able to receive input operations from the user via an operation acceptance unit 23 which will be discussed later.

The pattern selection unit 11, in the present embodiment, receives a fasting blood sugar level input by the user, via the operation acceptance unit 23 discussed later, and selects one time series pattern best suited to the user from the time series patterns stored in the pattern database 13, based on the received fasting blood sugar level.

Also, in the present embodiment, the "fasting blood sugar level" desirably is the blood sugar level of blood collected from the user in a state where two hours or more have elapsed since he or she last ate. Specifically, an exemplary "fasting blood sugar level" is the blood sugar level of blood collected during a health check.

Also, in the present embodiment, an exemplary time series pattern is a set of functions set for every timeslot whose reference time is the fasting time of the user, with each function specifying a relationship between elapsed time from the reference time and blood sugar level. A specific example of a time series pattern is shown below. The following equations (1) to (16) are functions constituting one time series pattern.

$$\lambda = a_1 t + b_1 (0 < t \leq 1) \qquad (1)$$

$$\lambda = a_2 t + b_2 (1 < t \leq 2) \qquad (2)$$

$$\lambda = a_3 t + b_3 (2 < t \leq 3) \qquad (3)$$

$$\lambda = a_4 t + b_4 (3 < t \leq 4) \qquad (4)$$

$$\lambda = a_5 t + b_5 (4 < t \leq 5) \qquad (5)$$

$$\lambda = a_6 t + b_6 (5 < t \leq 6) \qquad (6)$$

$$\lambda = a_7 t + b_7 (6 < t \leq 7) \qquad (7)$$

$$\lambda = a_8 t + b_8 (7 < t \leq 8) \qquad (8)$$

$$\lambda = a_9 t + b_9 (8 < t \leq 9) \qquad (9)$$

$$\lambda = a_{10} t + b_{10} (9 < t \leq 10) \qquad (10)$$

$$\lambda = a_{11} t + b_{11} (10 < t \leq 11) \qquad (11)$$

$$\lambda = a_{12} t + b_{12} (11 < t \leq 12) \qquad (12)$$

$$\lambda = a_{13} t + b_{13} (12 < t \leq 13) \qquad (13)$$

$$\lambda = a_{14} t + b_{14} (13 < t \leq 14) \qquad (14)$$

$$\lambda = a_{15} t + b_{15} (14 < t \leq 15) \qquad (15)$$

$$\lambda = a_{16} t + b_{16} (15 < t \leq 16) \qquad (16)$$

As shown in the above equations (1) to (16), the time series pattern is constituted by a plurality of linear functions set for every hour. In each linear function, $\lambda$ denotes the blood sugar level, and $a_1$ to $a_{16}$ and $b_1$ to $b_{16}$ denote arbitrary constants. Also, t indicates the elapsed time (in hours) from the user's fasting time (reference time: t=0). Note that if the "fasting blood sugar level" is measured from blood collected during a health check or the like when the user is in a fasting state, the "fasting time" (reference time) specifically means the time at which the blood was collected.

Also, in the present embodiment, in order to enhance the accuracy with which the time series pattern is selected, the pattern selection unit 11 preferably also selects a time series pattern using the blood sugar level of the user after eating, in addition to the blood sugar level at the time of fasting. Here, the criteria for selecting a time series pattern will be described using FIG. 2.

Figure 2:
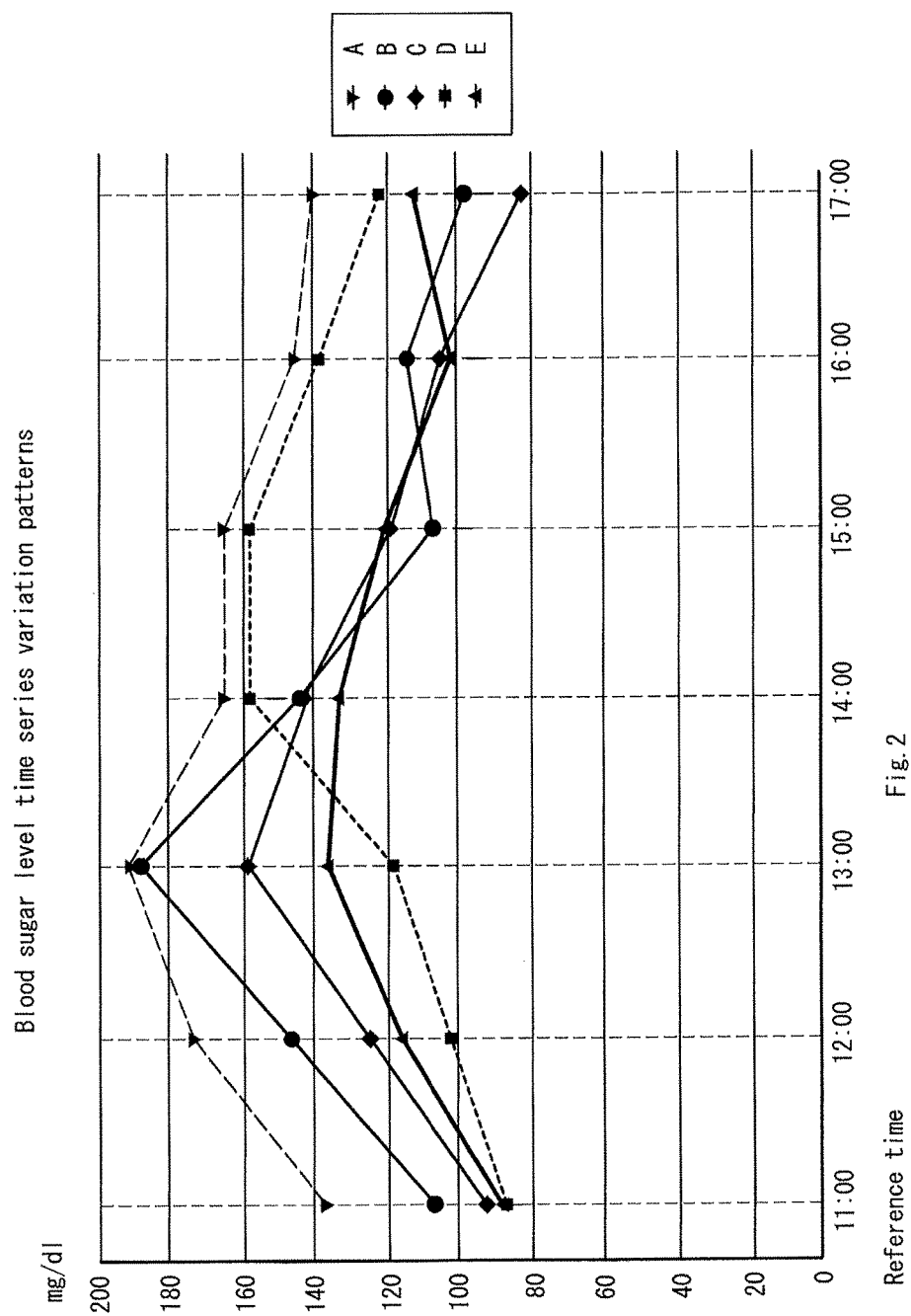
FIG. 2 shows exemplary time series variation patterns of typical blood sugar levels.

FIG. 2 shows exemplary time series variation patterns of typical blood sugar levels. In FIG. 2, graphs A to E respectively show examples of time series variation patterns. Note that, in FIG. 2, only the patterns for the first six hours from the reference time are shown.

Specifically in FIG. 2, graph A shows a time series variation pattern in which the fasting blood sugar level is 120 mg/dl or more. In the case where the user is diabetic, the time series variation pattern will be the same as or similar to graph A.

Graphs B and C show time series variation patterns in which the fasting blood sugar level is less than 120 mg/dl but the blood sugar level rises rapidly in the first hour after eating and is 140 mg/dl or more even two hour later. In the case of a person with postprandial hyperglycemia who is at risk of becoming diabetic, the time series variation pattern will be the same as or similar to either graph B or C.

Graph D shows a time series variation pattern in which the fasting blood sugar level is less than 120 mg/dl and the blood sugar level does not rise rapidly in the first hour after eating but reaches 140 mg/dl or more two hour later. In the case where the user is diabetic and is already under medication, the time series variation pattern will be the same as or similar to graph D.

Graph E shows a time series variation pattern in which the fasting blood sugar level is less than 120 mg/dl and the blood sugar level rises in the first one to two hours after eating but remains under 140 mg/dl. In the case where the user is healthy, the time series variation pattern will be the same as or similar to graph E.

Accordingly, if the blood sugar level after eating (e.g., two hours after eating) is used in addition to the fasting blood sugar level, the pattern selection unit 11 is able to reliably select the time series variation pattern best suited to the user from the five time series patterns of graphs A to E, as evident from FIG. 2. Also, in the present embodiment, the method of measuring the blood sugar level after eating is not particularly limited, and the blood sugar level after eating may be measured by a measurement unit 22.

Also, the correction processing unit 12, in the present embodiment, first accesses a measured value database 25 and extracts the measured value obtained with each optical measurement by the measurement unit 22 and the measurement date-time thereof. Furthermore, the correction processing unit 12 converts the measurement time of the extracted measurement date-time into an elapsed time t from the reference time.

Next, the correction processing unit 12 corrects the initial pattern by applying the least-squares method to the measured values. Specifically, the correction processing unit 12 derives, for each measured value having the same elapsed time t, the square root of the residual error between the measured value and a value (blood sugar level $\lambda$) calculated by applying the converted elapsed time t to each linear function of the initial pattern, and furthermore, corrects each linear function of the initial pattern such that when the square roots are summed, the sum is minimized.

As a result, each linear function of the initial pattern more correctly represents the actual condition of the user 30. Also, the correction processing unit 12 stores the corrected time series pattern in the measured value database 25.

Also, the setting condition determination unit 14 determines whether the measured values satisfy a set condition, after a set time period has elapsed since selection of the time series pattern by the pattern selection unit 11. Specifically, an exemplary set time period is a period conceivably taken for a change to appear in a person's blood sugar level in the case where the person becomes diabetic, such as two months, for example.

Furthermore, exemplary set conditions include a sufficient number of data (e.g., 20 pieces or more) being stored in the measured value database 25 during the set period, and the error between the uncorrected time series variation pattern and the measured values falling within a certain range (e.g., within ±10%). Note that the set conditions are not limited to the abovementioned conditions, and need only be conditions that can specify a change in the user's condition that requires selection of a time series variation pattern to be executed again.

Also, in the case where it is determined by the set condition determination unit 14 that the measured values do not meet the set conditions, selection of a time series pattern is executed again by the pattern selection unit 11, and correction of the newly selected time series pattern is executed by the correction processing unit 12. Performing the determination processing by the set condition determination unit 14 thus enables a flexible response even in the case where the user's health changes.

Next, the configuration of the measurement device 20 will be described. As shown in FIG. 1, the measurement device 20 is provided with a control processing unit 21, a measurement unit 22, an operation acceptance unit 23 for accepting input operations from the user 30, a standard curve database 24, a measured value database 25, and a display device 26 such as a liquid crystal panel, in addition to the blood sugar level prediction device 10.

The measurement unit 22 executes optical measurement. Although not specifically illustrated, the measurement unit 22 is provided with optical components such as a light source that emits light of a set wavelength, a light receiving element that receives light reflected by a part of the user 30 (finger, etc.), an optical filter, and a lens. Note that the configuration of the measurement unit 22 is not particularly limited, and the measurement unit 22 can be constituted by an existing component or the like.

Also, the measurement unit 22, in the present embodiment, executes optical measurement in response to an instruction from the control processing unit 21, and outputs data obtained from execution of the optical measurement, specifically, data (output signal of light receiving element) that specifies the intensity of light received by the light receiving element, to the control processing unit 21.

The standard curve database 24 stores standard curves for converting measured values that are obtained from execution of the optical measurement into blood sugar levels. A standard curve is created by executing optical measurement and blood sugar level measurement on a sample prepared in advance and deriving the relationship between obtained absorbances and blood sugar levels. Also, because the optimal standard curve differs depending on the values of the blood sugar levels, a plurality of standard curves are created according to the values of the blood sugar levels. In other words, a plurality of standard curves having different target ranges of blood sugar levels are created, and these curves are stored in the standard curve database 24. Note that blood sugar level measurement for creating standard curves is performed by a measurement method other than optical measurement.

The control processing unit 21, upon a measurement start operation by the user 30 being received by the operation acceptance unit 23, instructs the measurement unit 22 to execute optical measurement. The control processing unit 21, upon receiving data output from the measurement unit 22, then calculates the absorbance based on this data. Furthermore, the control processing unit 21 acquires a standard curve from the standard curve database 24, applies the calculated absorbance to the acquired standard curve, and calculates the blood sugar level (measured value). Furthermore, the control processing unit 21 stores the obtained blood sugar level (measured value) in the measured value database 25 in association with the date-time of the measurement.

Also, the control processing unit 21 is able to acquire measured values and measurement date-times from the measured value database 25, and display this data on the display device 26. Furthermore, in the present embodiment, the measured values and measurement date-times stored in the measured value database 25 are used in correction processing by the correction processing unit 12.

Also, in the present embodiment, in the case where selection and correction of a time series pattern have been executed by the blood sugar level prediction device 10, the control processing unit 21 of the measurement device 20 predicts the blood sugar level utilizing the time series variation pattern, and selects an optimal standard curve based on the predicted blood sugar level.

Specifically, the control processing unit 21 first acquires a corrected time series pattern stored in the measured value database 25, selects a linear function corresponding to the time of the measurement from the acquired time series pattern, and calculates the blood sugar level using the selected linear function. Next, the control processing unit 21 specifies the standard curve corresponding to the calculated blood sugar level from among the standard curves stored in the standard curve database 24, and acquires the specified standard curve. According to the present embodiment, improvement in the measurement accuracy of the measurement device 20 is also achieved, because the optimal standard curve can be readily specified.

Device Operations

Next, operations of the blood sugar level prediction device 10 of the present embodiment will be described using FIGS. 3 to 6. Also, in the following description, FIGS. 1 and 2 are referred to as appropriate. Furthermore, in the present embodiment, the blood sugar level prediction method is implemented by operating the blood sugar level prediction device 10. Therefore, the following description of the operations of the blood sugar level prediction device is given in place of a description of the blood sugar level prediction method of the present embodiment.

Selection and Correction of Time Series Pattern

Figure 3:
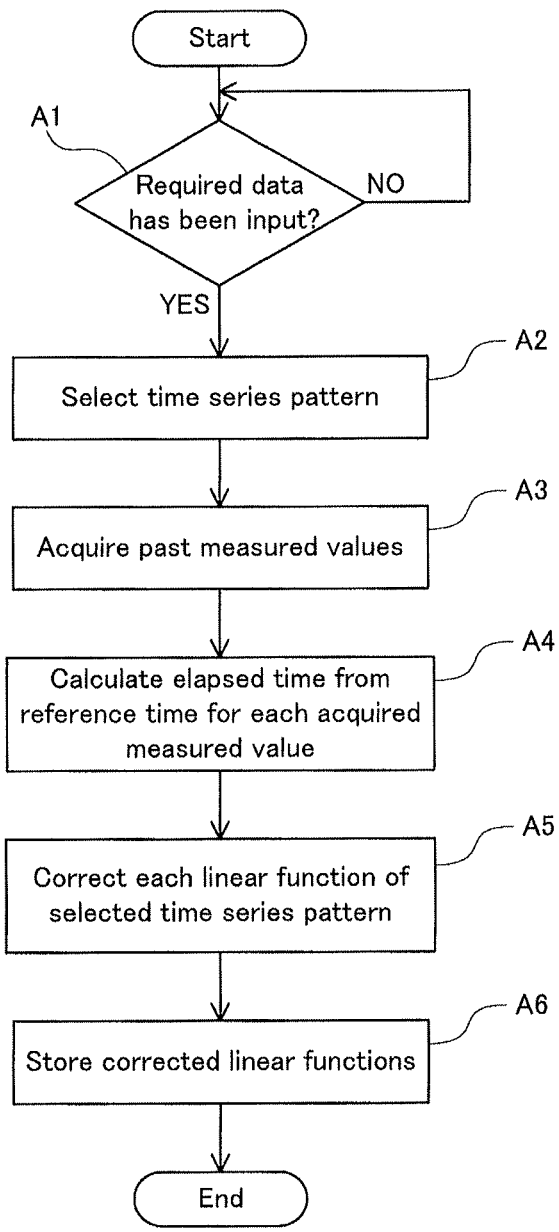
FIG. 3 is a flow diagram showing processing for selecting and correcting a time series pattern by the blood sugar level prediction device in the embodiment of the present invention.

Initially, selection and correction of a time series pattern by the blood sugar level prediction device 10 will be described using FIG. 3. FIG. 3 is a flow diagram showing processing for selecting and correcting a time series pattern by the blood sugar level prediction device according to the present embodiment.

As shown in FIG. 3, initially, in the blood sugar level prediction device 10, the pattern selection unit 11 determines whether required data, specifically, a fasting blood sugar level and a blood sugar level after eating have been input via the operation acceptance unit 23 (step A1).

If the result of the determination of step A1 indicates that the required data has not been input, the pattern selection unit 11 enters a standby state. On the other hand, if the result of the determination of step A1 indicates that the required data has been input, the pattern selection unit 11 accesses the pattern database 13, and selects one time series pattern best suited to the user 30, based on the fasting blood sugar level and the blood sugar level after eating (step A2).

Next, once step A2 is executed, the correction processing unit 12 accesses the measured value database 25, and extracts the measured value obtained with each optical measurement by the measurement unit 22, and the measurement date-time thereof (step A3). Also, at step A3, conditions may be set for extraction of measured values and measurement date-times by the correction processing unit 12.

Specifically, exemplary conditions include the period from the oldest measurement date-time to the most recent measurement date-time being a period conceivably taken for a change to appear in the blood sugar level in the case where the user become diabetic, such as two months, for example, and a sufficient number of data (e.g., 20 pieces or more) being extracted.

Next, the correction processing unit 12 converts the measurement time of every extracted measurement date-time into an elapsed time t from the reference time (step A4). Then, the correction processing unit 12 corrects the initial pattern by applying the least-squares method to the measured values (step A5). Specifically, the correction processing unit 12 derives, for each measured value having the same elapsed time t, the square root of the residual error between the measured value and a value calculated by applying the elapsed time t to each linear function of the initial pattern, and corrects the slope and the intercept of each linear function such that when the square roots are summed, the sum is minimized.

Thereafter, the correction processing unit 12 stores each corrected linear function in the measured value database 25 (step A6). Once step A6 is executed, the processing in the blood sugar level prediction device 10 ends. Thereafter, the corrected initial pattern (linear functions) stored in the measured value database 25 is utilized in the selection of a standard curve by the control processing unit 21.

As mentioned above, once steps A1 to A6 are executed, the time series variation pattern closest to the time series variation in the blood sugar level of the user 30 is selected, and, furthermore, this initial pattern is corrected with actual measured values. Accordingly, a time series variation pattern that is aligned with the actual condition of the user 30 is readily obtained, enabling the blood sugar level of the user 30 to be correctly predicted while reducing the burden on the user 30.

Figure 4:
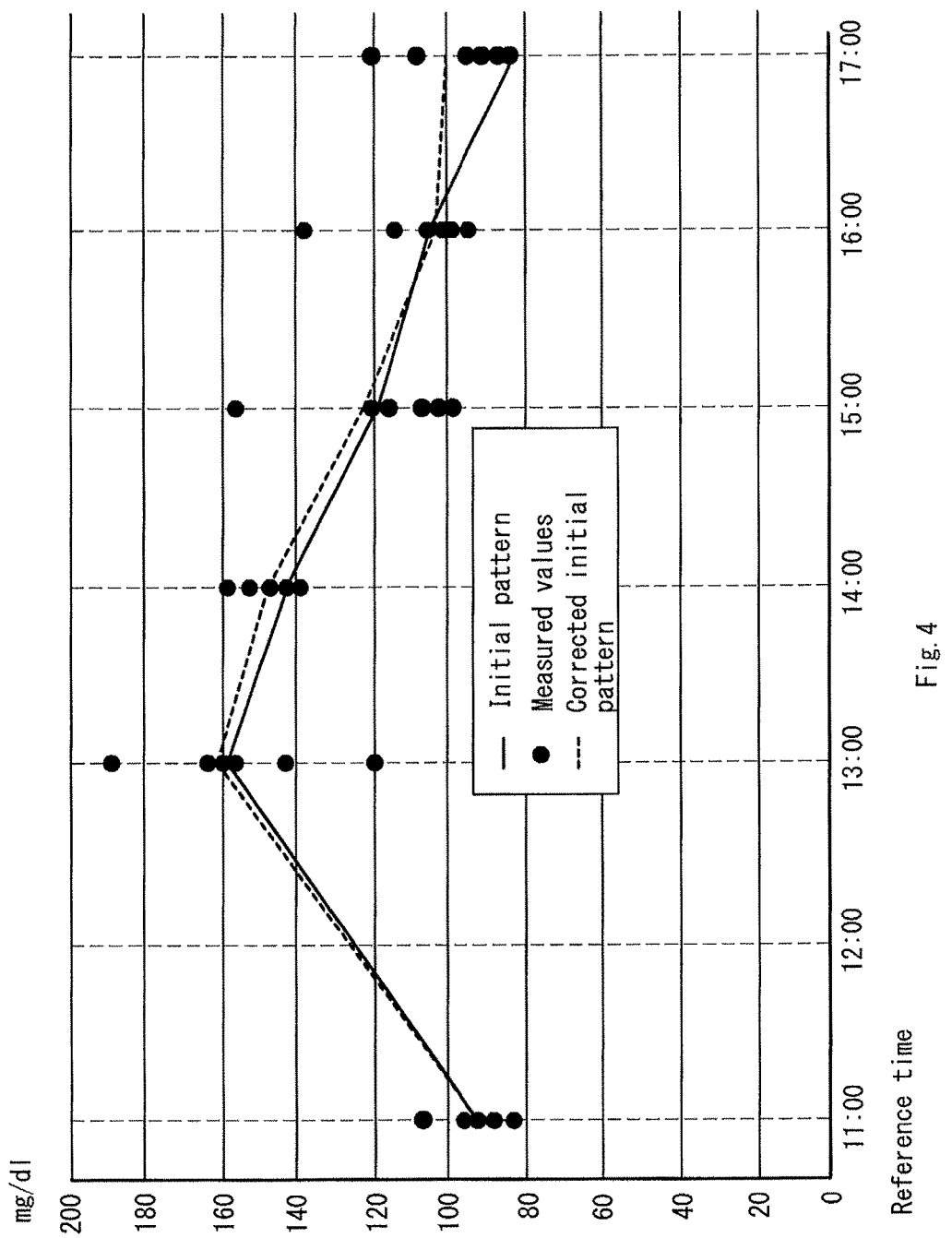
FIG. 4 shows an example of a corrected initial pattern in the embodiment of the present invention.

Here, a specific example of initial pattern correction will be described using FIG. 4. FIG. 4 shows an example in which the initial pattern has been corrected in the present embodiment. As shown in FIG. 4, in the case where an initial pattern shown with the solid line is selected, the corrected initial pattern will be as shown with the dashed line, assuming that the measurement results shown with the circles are obtained.

Reselection of Time Series Pattern

Figure 5:
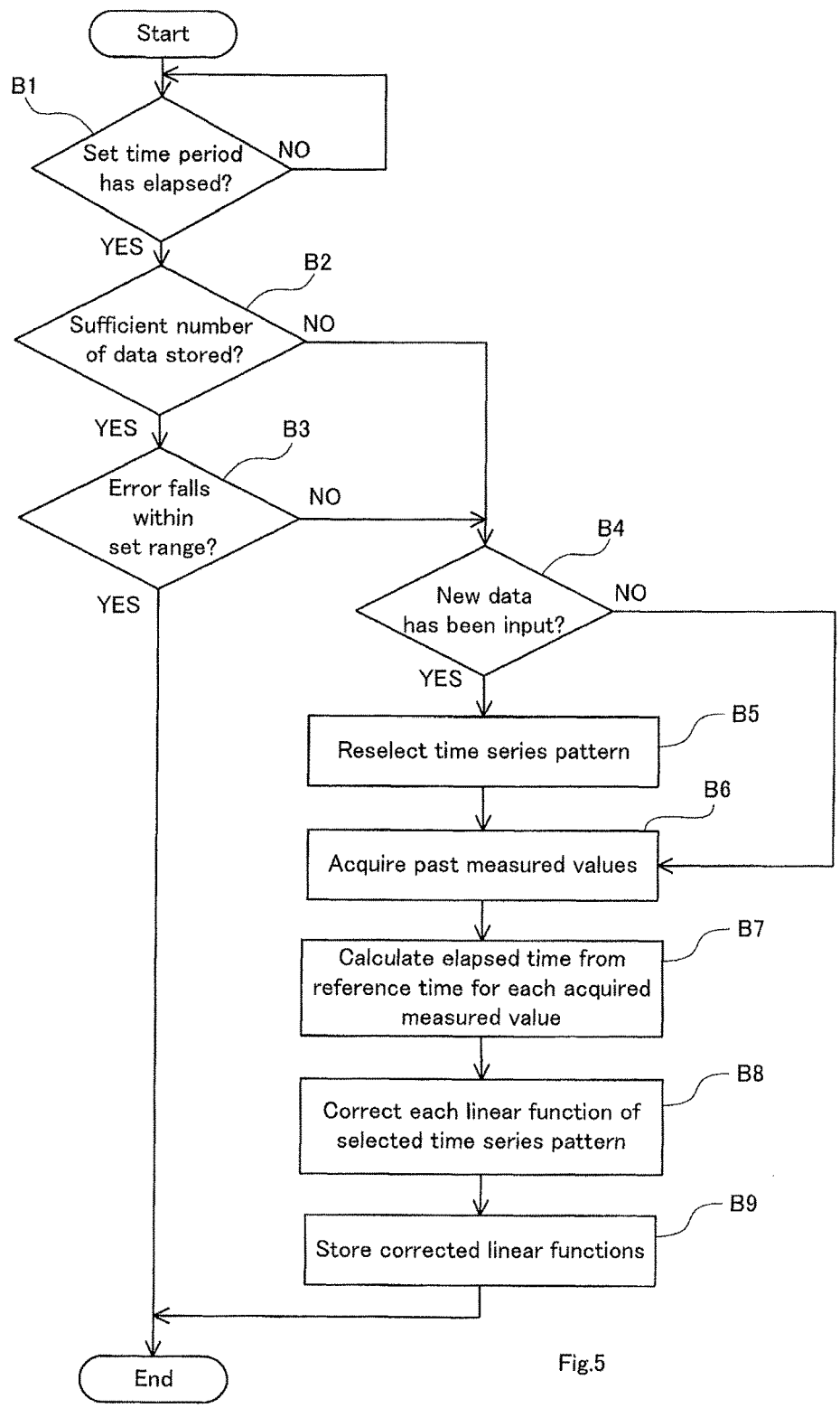
FIG. 5 is a flow diagram showing processing for reselecting a time series pattern by the blood sugar level prediction device in the embodiment of the present invention.

Then, reselection of a time series pattern by the blood sugar level prediction device 10 will be described using FIG. 5. FIG. 5 is a flow diagram showing processing for reselecting a time series pattern by the blood sugar level prediction device according to the present embodiment.

As shown in FIG. 5, initially, in the blood sugar level prediction device 10, the set condition determination unit 14 determines whether the set period has elapsed since selection of the time series pattern by the pattern selection unit 11 (step B1).

If the result of the determination of step B1 indicates that the set period has not elapsed, the set condition determination unit 14 enters a standby state. On the other hand, if the result of the determination of step B1 indicates that the set period has elapsed, the set condition determination unit 14 determines whether the number of data stored in the measured value database 25 within the set period is greater than or equal to a set value (e.g., 20 pieces) (step B2).

If the result of the determination of step B2 indicates that the number of data is less than the set value, step B4 is executed. On the other hand, if the result of the determination of step B2 indicates that the number of data is greater than or equal to the set value, the set condition determination unit 14 determines whether the error between the uncorrected initial pattern and the measured values falls within a set range (e.g., ±10%) (step B3).

If the result of the determination of step B3 indicates that the error between the uncorrected initial pattern and the measured values does not fall within the set range, step B4 is executed. On the other hand, if the result of the determination of step B3 indicates that the error between the uncorrected initial pattern and the measured values falls within the set range, the set condition determination unit 14 ends the processing.

In step B4, the pattern selection unit 11 determines whether a fasting blood sugar level and a blood sugar level after eating have been newly input via the operation acceptance unit 23. If the result of step B4 indicates that a fasting blood sugar level and a blood sugar level after eating have not been newly input, step B6 is executed.

On the other hand, if the result of step B4 indicates that a fasting blood sugar level and a blood sugar level after eating have been newly input, the pattern selection unit 11 again selects a time series pattern best suited to the user 30, based on the newly input blood sugar levels (step B5).

If blood sugar levels have not been newly input at step B4 or if step B5 has been executed, the correction processing unit 12 executes steps B6 to B9. As a result, the initial pattern or the reselected initial pattern will be the pattern best suited to the user 30. Note that steps B6 to B9 respectively correspond to steps A3 to A6 shown in FIG. 3.

As described above, executing steps B1 to B9 enables a flexible response even in the case where the health of the user 30 changes. It is thus possible to predict the blood sugar level of the user 30, even in the case where a healthy user 30 becomes diabetic.

Optical Measurement

Figure 6:
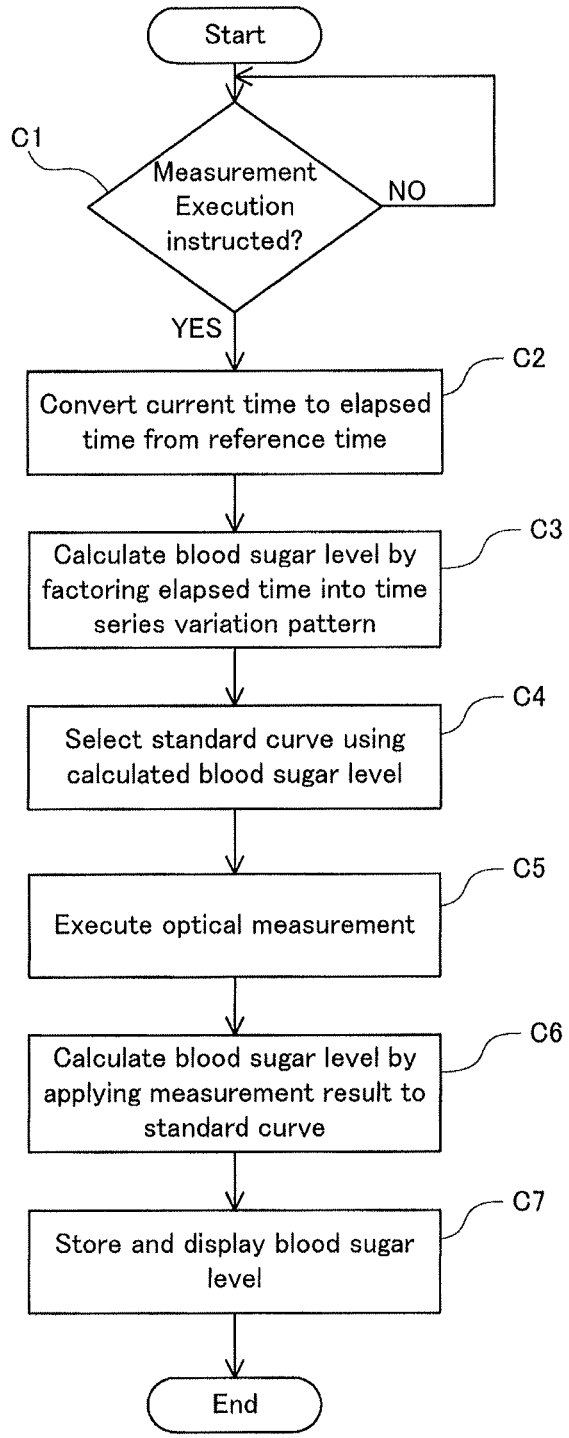
FIG. 6 is a flow diagram showing operations of the measurement device in the embodiment of the present invention.

Here, operations of the measurement device 20 of the present embodiment will be described using FIG. 6. FIG. 6 is a flow diagram showing operations of the measurement device of the present embodiment.

As shown in FIG. 6, in the measurement device 20, the control processing unit 21 first determines whether a measurement start operation by the user 30 has been received by the operation acceptance unit 23 (step C1).

If the result of the determination of step C1 indicates that a measurement start operation has not been received, the control processing unit 21 enters a standby state. On the other hand, if the result of the determination of step C1 indicates that a measurement start operation has been received, the control processing unit 21 converts the current time into an elapsed time t from the reference time (step C2).

Next, the control processing unit 21 acquires a corrected time series variation pattern from the measured value database 25, and calculates the blood sugar level by factoring the calculated elapsed time t into the acquired time series variation pattern (step C3). Then, the control processing unit 21 accesses the standard curve database 24, selects an optimal standard curve using the blood sugar level calculated at step C3, and acquires the selected standard curve (step C4).

Next, the control processing unit 21 instructs the measurement unit 22 to execute optical measurement (step C5). The measurement unit 22 thereby irradiates a part of the user 30 with light, and, furthermore, receives reflected light reflected by the user 30 and outputs data specifying the intensity of the reflected light that is received to the control processing unit 21.

Next, the control processing unit 21 calculates the absorbance from the result of the optical measurement of step C5, and calculates the blood sugar level by applying the calculated absorbance to the standard curve selected at step C4 (step C6). Thereafter, the control processing unit 21 stores the blood sugar level calculated at step C6 in the measured value database 25 in association with the measurement date-time of the measurement, and displays the measured value and the measurement date-time on the display device 26 (step C7).

As mentioned above, executing steps C1 to C7 enables an optimal standard curve to be readily selected, thus leading to an improvement in the measurement accuracy of the measurement device 20.

Computer Program

A computer program of the present embodiment need only be a program that causes a computer to execute steps A1 to A6 shown in FIG. 3 and steps B1 to B9 shown in FIG. 5. Also, in the present embodiment, exemplary computers include a computer mounted in a device such as a measurement device or, furthermore, a general-purpose personal computer.

The blood sugar level prediction device and the blood sugar level prediction method of the present embodiment can be realized by installing such a program in a computer and executing the program. In this case, a CPU (Central Processing Unit) of the computer performs processing while functioning as the pattern selection unit 11, the correction processing unit 12 and the set condition determination unit 14.

Also, the program of the present embodiment may be a program that causes a computer to execute steps C1 to C7 shown in FIG. 6. In this case, the measurement device of the present embodiment can be realized, and a CPU (Central Processing Unit) of the computer performs processing while functioning as the control processing unit 21.

Note that the program of the present embodiment may be circulated on the Internet or may be provided in a state of being stored on a computer-readable storage medium. Specific examples of the storage medium include a general-purpose semiconductor memory device such as CF (Compact Flash (registered trademark)) or SD (Secure Digital), a magnetic storage medium such as a flexible disk, or an optical storage medium such as CD-ROM (Compact Disk Read Only Memory).

Although the instant invention has been described above with reference to an embodiment, the invention is not intended to be limited to the above embodiment. A person skilled in the art will appreciate that the configurations and details of the instant invention can be variously modified within the scope of the invention.

This application claims priority from Japanese Patent Application No. 2012-265283 filed on Dec. 4, 2012, the entire disclosure of which is herein incorporated by reference.

Although the abovementioned embodiment can be partially or wholly represented by supplementary notes 1 to 13 described below, the present invention is not limited to the following description.

Supplementary Note 1

A blood sugar level prediction device for predicting a user's blood sugar level is provided with a pattern selection unit that selects one pattern from a plurality of preset blood sugar level time series variation patterns, based on a blood sugar level at a fasting time of the user, and a correction processing unit that corrects the selected pattern using a plurality of measured values obtained by executing optical measurement of blood sugar levels over a number of measurement dates, targeting the user.

Supplementary Note 2

In the blood sugar level prediction device according to supplementary note 1, the pattern selection unit selects the pattern using a blood sugar level after eating in addition to the blood sugar level at the fasting time of the user.

Supplementary Note 3

In the blood sugar level prediction device according to supplementary note 1, the plurality of patterns each include a set of functions that are set for every timeslot whose reference time is the fasting time of the user and that specify a relationship between elapsed time from the reference time and blood sugar level, and the correction processing unit converts a measurement time of the optical measurement into an elapsed time from the reference time, derives, for each of the plurality of measured values, a square root of a residual error between the measured value and a value calculated by applying the converted elapsed time to the functions of the selected pattern, and corrects each of the functions of the selected time series variation pattern such that when the square roots are summed, the sum is minimized.

Supplementary Note 4

The blood sugar level prediction device according to supplementary note 1 is further provided with a set condition determination unit that determines, after a set time period has elapsed since selection of the pattern, whether the measured values obtained by the optical measurement of blood sugar levels that targeted the blood of the user meet a set condition, and if it is determined by the set condition determination unit that the obtained measured values do not meet the set condition, the pattern selection unit executes selection of the pattern again and the correction processing unit corrects the newly selected pattern.

Supplementary Note 5

A measurement device that measures a blood sugar level of a user through optical measurement is provided with a measurement unit that executes the optical measurement, a standard curve database that stores a standard curve for converting a measured value that is obtained by executing the optical measurement into a blood sugar level, for each value of corresponding blood sugar levels, a control processing unit that calculates a blood sugar level by selecting one of the standard curves and applying the measured value obtained by executing the optical measurement to the selected standard curve, and a blood sugar level prediction unit that predicts the blood sugar level of the user by selecting one pattern from a plurality of preset blood sugar level time series variation patterns, based on a blood sugar level at a fasting time of the user, and correcting the selected pattern using a plurality of measured values obtained by executing the optical measurement over a number of measurement dates, targeting the user, the control processing unit, in a case where selection and correction of the pattern have been executed by the blood sugar level prediction unit, predicting the blood sugar level using the corrected pattern and selecting the standard curve based on the predicted blood sugar level.

Supplementary Note 6

A method for predicting a user's blood sugar level has the steps of (a) selecting one pattern from a plurality of preset blood sugar level time series variation patterns, based on a blood sugar level at a fasting time of the user, and (b) correcting the selected pattern using a plurality of measured values obtained by executing optical measurement of blood sugar levels over a number of measurement dates, targeting the user.

Supplementary Note 7

In the blood sugar level prediction method according to supplementary note 6, the step (a) comprises selecting the pattern using a blood sugar level after eating in addition to the blood sugar level at the fasting time of the user.

Supplementary Note 8

In the blood sugar level prediction method according to supplementary note 6, the plurality of patterns each include a set of functions that are set for every timeslot whose reference time is the fasting time of the user and that specify a relationship between elapsed time from the reference time and blood sugar level, and the step (b) comprises converting a measurement time of the optical measurement into an elapsed time from the reference time, deriving, for each of the plurality of measured values, a square root of a residual error between the measured value and a value calculated by applying the converted elapsed time to the functions of the selected pattern, and correcting each of the functions of the selected time series variation pattern such that when the square roots are summed, the sum is minimized.

Supplementary Note 9

The blood sugar level prediction method according to supplementary note 6 further has the step of (c) determining, after a set time period has elapsed since selection of the pattern, whether the measured values obtained by the optical measurement of blood sugar levels that targeted the blood of the user meet a set condition, and if it is determined in the step (c) that the obtained measured values do not meet the set condition, the step (a) and the step (b) are executed again.

Supplementary Note 10

A computer-readable storage medium stores a computer program for predicting a blood sugar level of a user by computer, the program including a command for causing the computer to execute the steps of (a) selecting one pattern from a plurality of preset blood sugar level time series variation patterns, based on a blood sugar level at a fasting time of the user, and (b) correcting the selected pattern using a plurality of measured values obtained by executing optical measurement of blood sugar levels over a number of measurement dates, targeting the user.

Supplementary Note 11

In the computer-readable storage medium according to supplementary note 10, the step (a) comprises selecting the pattern using a blood sugar level after eating in addition to the blood sugar level at the fasting time of the user.

Supplementary Note 12

In the computer-readable storage medium according to supplementary note 10, the plurality of patterns each include a set of functions that are set for every timeslot whose reference time is the fasting time of the user and that specify a relationship between elapsed time from the reference time and blood sugar level, and the step (b) comprises converting a measurement time of the optical measurement into an elapsed time from the reference time, deriving, for each of the plurality of measured values, a square root of a residual error between the measured value and a value calculated by applying the converted elapsed time to the functions of the selected pattern, and correcting each of the functions of the selected time series variation pattern such that when the square roots are summed, the sum is minimized.

Supplementary Note 13

In the computer-readable storage medium according to supplementary note 10, the program further includes a command that causes the computer to execute the step of (c) determining, after a set time period has elapsed since selection of the pattern, whether the measured values obtained by the optical measurement of blood sugar levels that targeted the blood of the user meet a set condition, and if it is determined in the step (c) that the obtained measured values do not meet the set condition, the step (a) and the step (b) are executed again.

INDUSTRIAL APPLICABILITY

According to the present invention, the user's blood sugar level can be correctly predicted, while reducing the burden on the user at the time of blood sugar level measurement. The present invention is useful in a measurement device or a medical system that measures blood sugar levels.

DESCRIPTION OF REFERENCE NUMERALS

10 Blood sugar level prediction device
11 Pattern selection unit
12 Correction processing unit
13 Pattern database
14 Set condition determination unit
20 Measurement device
21 Control processing unit
22 Measurement unit
23 Operation acceptance unit
24 Standard curve database
25 Measured value database
26 Display device
30 User

The invention claimed is:

1. A blood sugar level prediction device for predicting a blood sugar level of a user, the blood sugar level prediction device comprising a computer processor that realizes:
   a pattern selection unit that selects one pattern from a plurality of preset blood sugar level time series variation patterns, based on a blood sugar level at a fasting time of the user; and
   a correction processing unit that corrects the selected pattern using a plurality of measured values obtained by executing optical measurement of blood sugar levels over a number of measurement dates, targeting the user,
   wherein the computer processor further realizes:
   a set condition determination unit that determines, after a set time period has elapsed since selection of the pattern, whether the measured values obtained by the optical measurement of blood sugar levels that targeted the blood of the user meet a set condition,
   wherein if it is determined by the set condition determination unit that the obtained measured values do not meet the set condition, the pattern selection unit executes selection of the pattern again and the correction processing unit corrects the newly selected pattern.

2. The blood sugar level prediction device according to claim 1,
   wherein the pattern selection unit selects the pattern using a blood sugar level after eating in addition to the blood sugar level at the fasting time of the user.

3. The blood sugar level prediction device according to claim 1,
   wherein the plurality of patterns each include a set of functions that are set for every timeslot whose reference time is the fasting time of the user and that specify a relationship between elapsed time from the reference time and blood sugar level, and
   the correction processing unit converts a measurement time of the optical measurement into an elapsed time from the reference time, derives, for each of the plurality of measured values, a square root of a residual error between the measured value and a value calculated by applying the converted elapsed time to the functions of the selected pattern, and corrects each of the functions of the selected time series variation pattern such that when the square roots are summed, the sum is minimized.

4. A measurement device that measures a blood sugar level of a user through optical measurement, comprising:

a measurement unit that executes the optical measurement;

a standard curve database that stores a standard curve for converting a measured value that is obtained by executing the optical measurement into a blood sugar level, for each size of corresponding blood sugar levels;

a control processing unit that calculates a blood sugar level by selecting one of the standard curves and applying the measured value obtained by executing the optical measurement to the selected standard curve; and a blood sugar level prediction unit that predicts the blood sugar level of the user by selecting one pattern from a plurality of preset blood sugar level time series variation patterns, based on a blood sugar level at a fasting time of the user, and correcting the selected pattern using a plurality of measured values obtained by executing the optical measurement over a number of measurement dates, targeting the user, wherein the control processing unit, in a case where selection and correction of the pattern have been executed by the blood sugar level prediction unit, predicts the blood sugar level using the corrected pattern and selects the standard curve based on the predicted blood sugar level, and wherein a set condition determination unit determines, after a set time period has elapsed since selection of the pattern, whether the measured values obtained by the optical measurement of blood sugar levels that targeted the blood of the user meet a set condition, wherein if it is determined by the set condition determination unit that the obtained measured values do not meet the set condition, the blood sugar level prediction unit executes selection of the pattern again and correction of the newly selected pattern.

5. A blood sugar level prediction method for predicting a blood sugar level of a user, comprising the steps of:
(a) selecting, by a computer, one pattern from a plurality of preset blood sugar level time series variation patterns, based on a blood sugar level at a fasting time of the user;
(b) correcting, by the computing, the selected pattern using a plurality of measured values obtained by executing optical measurement of blood sugar levels over a number of measurement dates, targeting the user, and
(c) determining, by the computer, after a set time period has elapsed since selection of the pattern, whether the measured values obtained by the optical measurement of blood sugar levels that targeted the blood of the user meet a set condition,
wherein if it is determined in the step (c) that the obtained measured values do not meet the set condition, the step (a) and the step (b) are executed again.

6. The blood sugar level prediction method according to claim 5,
wherein the step (a) comprises selecting the pattern using a blood sugar level after eating in addition to the blood sugar level at the fasting time of the user.

7. The blood sugar level prediction method according to claim 5,
wherein the plurality of patterns each include a set of functions that are set for every timeslot whose reference time is the fasting time of the user and that specify a relationship between elapsed time from the reference time and blood sugar level, and
the step (b) comprises converting, by the computer, a measurement time of the optical measurement into an elapsed time from the reference time, deriving, by the computer, for each of the plurality of measured values, a square root of a residual error between the measured value and a value calculated by applying the converted elapsed time to the functions of the selected pattern, and correcting, by the computer, each of the functions of the selected time series variation pattern such that when the square roots are summed, the sum is minimized.

8. A non-transitory computer-readable storage medium storing a computer program executed by a processor for predicting a blood sugar level of a user by computer, the processor executing the program to perform the steps of:
(a) selecting one pattern from a plurality of preset blood sugar level time series variation patterns, based on a blood sugar level at a fasting time of the user;
(b) correcting the selected pattern using a plurality of measured values obtained by executing optical measurement of blood sugar levels over a number of measurement dates, targeting the user; and
(c) determining, after a set time period has elapsed since selection of the pattern, whether the measured values obtained by the optical measurement of blood sugar levels that targeted the blood of the user meet a set condition, and
if it is determined in the step (c) that the obtained measured values do not meet the set condition, the step (a) and the step (b) are executed again.

9. The non-transitory computer-readable storage medium according to claim 8,
wherein the step (a) comprises selecting the pattern using a blood sugar level after eating in addition to the blood sugar level at the fasting time of the user.

10. The non-transitory computer-readable storage medium according to claim 8,
wherein the plurality of patterns each include a set of functions that are set for every timeslot whose reference time is the fasting time of the user and that specify a relationship between elapsed time from the reference time and blood sugar level, and
the step (b) comprises converting a measurement time of the optical measurement into an elapsed time from the reference time, deriving, for each of the plurality of measured values, a square root of a residual error between the measured value and a value calculated by applying the converted elapsed time to the functions of the selected pattern, and correcting each of the functions of the selected time series variation pattern such that when the square roots are summed, the sum is minimized.

* * * * *